(12) United States Patent
Hirschel et al.

(10) Patent No.: US 9,278,178 B2
(45) Date of Patent: Mar. 8, 2016

(54) ROTATABLE GUIDE SLEEVE WITH SPRING SECURED TO PREVENT EXCESSIVE TENSIONING

(75) Inventors: Juerg Hirschel, Aarau (CH); Ulrich Moser, Heimiswil (CH); Christian Schrul, Lyssach (CH); Markus Tschirren, Kirchberg (CH)

(73) Assignee: TecPharma Licensing AG, Burgdorf (CH)

( * ) Notice: Subject to any disclaimer, the term of this patent is extended or adjusted under 35 U.S.C. 154(b) by 744 days.

(21) Appl. No.: 12/777,567

(22) Filed: May 11, 2010

(65) Prior Publication Data

US 2010/0312196 A1    Dec. 9, 2010

Related U.S. Application Data

(63) Continuation of application No. PCT/EP2008/009543, filed on Nov. 12, 2008.

(30) Foreign Application Priority Data

Nov. 12, 2007 (DE) .......................... 10 2007 053 743

(51) Int. Cl.
*A61M 5/315* (2006.01)
*A61M 5/20* (2006.01)
*A61M 5/24* (2006.01)

(52) U.S. Cl.
CPC ............. *A61M 5/31535* (2013.01); *A61M 5/20* (2013.01); *A61M 5/2448* (2013.01); *A61M 5/3155* (2013.01); *A61M 5/31533* (2013.01); *A61M 5/31553* (2013.01); *A61M 5/31561* (2013.01); *A61M 5/31583* (2013.01); *A61M 2005/202* (2013.01); *A61M 2205/581* (2013.01)

(58) Field of Classification Search
CPC .................. A61M 5/31535; A61M 5/31533; A61M 5/3155
USPC .................... 604/207, 208, 209, 210, 211
See application file for complete search history.

(56) References Cited

U.S. PATENT DOCUMENTS 5,626,566 A * 5/1997 Petersen ............ A61M 5/31551
222/309
2006/0276754 A1 12/2006 Kronestedt et al.

FOREIGN PATENT DOCUMENTS

| DE | 295 13 214 | 1/1997 |
| EP | 1 351 732 | 6/2005 |
| WO | WO 02/053214 | 7/2002 |

* cited by examiner

Primary Examiner — Kevin C Sirmons
Assistant Examiner — Shefali Patel
(74) Attorney, Agent, or Firm — Dorsey & Whitney, LLP; Stuart R. Hemphill, Esq.

(57) ABSTRACT

A dosing device for an injection device, including a dosing element moveable or rotatable in a first direction to select a dose and a guiding element for guiding a component of the injection device, the dosing element being moved or rotated relative to the guiding element to select the dose, wherein the guiding element is rotated or moved along with the dosing element when the dosing element is moved or rotated against the first direction to adjust the selected dose. A method of adjusting a dose selected by a dosing device is encompassed, the method including selecting the dose by moving or rotating a dosing element relative to a guiding element which is moved or rotated along with the dosing element during the selecting and adjusting the selected dose by moving or rotating the dosing element in an opposite direction.

9 Claims, 5 Drawing Sheets

ROTATABLE GUIDE SLEEVE WITH SPRING SECURED TO PREVENT EXCESSIVE TENSIONING

CROSS-REFERENCED RELATED APPLICATIONS

This application is a continuation of International Patent Application No. PCT/EP2008/009543 filed Nov. 12, 2008, which claims priority to German Patent Application No. DE 10 2007 053 743.5 filed Nov. 12, 2007, the entire contents of each are incorporated herein by reference.

BACKGROUND

The present invention relates to devices for delivering, administering, infusing, injecting or dispensing a substance, and to methods of making and using such devices. More particularly, the present invention relates to an injection device which enables a substance contained in the injection device, for example in an ampoule, to be dispensed in measured doses after setting or selecting a dose using the injection device or a feature thereof, the intention being that it should be easy to correct or adjust the set dose. More particularly, in some embodiments, the present invention relates to a dose setting device for use in combination with a container filled with fluid, wherein the dose setting device and/or the container are designed for repeatedly administering individually set or selected doses from the container.

A dose setting device which can be moved in two directions is known from documents EP 1 351 732 B and DE 2 951 321 4 U1.

SUMMARY

An object of the present invention is to provide a dose setting device for an injection device which offers a way of enabling a set dose to be corrected or adjusted, in other words, of resetting a dose that was, for example, set too high.

In one embodiment, the present invention comprises a dosing device for an injection device, including a dosing element moveable or rotatable in a first direction to select a dose and a guiding element for guiding a component of the injection device, the dosing element being moved or rotated relative to the guiding element to select a dose, wherein the guiding element is rotated or moved along with the dosing element when the dosing element is moved or rotated against the first direction to adjust the selected dose. A method of adjusting a dose selected by a dosing device is encompassed, the method including selecting a dose by moving or rotating a dosing element relative to a guiding element which is moved or rotated along with the dosing element during the selecting and adjusting the selected dose by moving or rotating the dosing element in the opposite direction.

In one embodiment the present invention comprises a dose setting device for an injection device, e.g. an automatic injection device with which a dose is dispensed automatically on initiating a dispensing operation. In one embodiment, the dose setting element comprises a dose setting element such as a dose setting sleeve which can be rotated relative to the dose setting device or the injection device connected to the dose setting device to set a dose. In this respect, the dose setting element may be mounted so that it is rotatable relative to the dose setting device or injection device and/or not able to move axially. However, in some embodiments, it is also possible to mount the dose setting element so that it can move in the axial direction, for example by providing a thread guide. The dose setting element is used to set a dose and there is a linear correlation between the setting distance or setting angle of the dose setting element and the set dose of the fluid to be dispensed from the injection device.

In some embodiments, a guide element is also provided, which is connected to the dose setting device or injection device so as to rotate in unison with it when setting a dose by rotating the dose setting element, for example. The guide element which, for example, might be a guide sleeve, is used to guide a plunger or threaded rod by means of an internal thread. The plunger or threaded rod is moved or screwed in the distal (or forward or injection) direction of the injection device, guided by the guide element, which is not able to move in the axial direction of the injection device to push on a stopper, for example, and thus cause a fluid to be dispensed. To set a dose, the dose setting element moves relative to the guide element, in other words rotates or moves in translation In some embodiments, the guide element is designed and mounted in the dose setting device or injection device and coupled with the dose setting element so that the guide element rotates in unison with the dose setting element during a setting or rotating movement to correct or adjust the dose set using the dose setting element, for example a rotating movement in the direction of rotation opposite that by or in which the dose is increased. For example, the guide element may be fitted or mounted in the dose setting device or injection device so that a correction movement or counter-rotating movement of the dose setting element is transmitted to the guide element, in which case the dose setting element and guide element are coupled during or in readiness for counter-rotating or correcting a setting and are locked to prevent a rotation and/or locked to prevent any translating movement relative to one another.

In one embodiment, the present invention relates to a dosing device for an injector, comprising a dosing element that can be moved or rotated in a first direction to adjust a dose, and an element for guiding a threaded bar, the dosing element being moved or rotated relative to the guiding element in order to adjust a dose. The invention is characterized in that the guiding element is rotated or moved along with the dosing element when the dosing element is moved or rotated against the first direction in order to correct or reduce the adjusted dose. The invention further relates to a method for correcting a dose adjusted by means of a dosing device. In said method, the dose is adjusted by moving or rotating a dosing element relative to a guiding element which is moved or rotated along with the dosing element when the dose is corrected by moving or rotating the dosing element in the opposite direction.

In some embodiments, the guide element can be released to correct the dose rather than being fixedly connected to the injection device or dose setting device. This enables a dose to be corrected essentially without the need for an engagement in the region of the dose setting device. Consequently, in accordance with some embodiments of the present invention, it is not necessary for the coupling between the dose setting element and the threaded rod to be released, for example, which simplifies the structural design of the dose setting device and hence the injection device.

In some preferred embodiments, the dose setting device has a threaded rod, e.g. a toothed and threaded rod, on which a thread is provided in the circumferential direction, either continuously or in part-sections, and the thread or individual thread portions have toothing comprising teeth extending in the axial direction or tooth part-sections. This threaded rod is guided in an internal thread of the guide element, and the guide element comprises at least one catch element which is able to co-operate with teeth of the rod so that a rotating movement of the rod is possible relative to the guide element in one direction (e.g. when dispensing a substance), but is locked, prevented or blocked in the opposite direction (e.g. when correcting a dose).

In some preferred embodiments, the dose setting element is coupled with a coupling element so as to rotate in unison with it so that a rotation of the dose setting element can be transmitted to the coupling element. The coupling element may have print on its external face in the circumferential direction, from which the set dose can be read through a viewing window, and the coupling element therefore serves as a display barrel. The coupling element is able to move in the axial direction relative to the dose setting element and has an internal thread or external thread, for example, which is guided in a co-operating complementary thread of the injection device or dose setting device to produce an axial displacement of the coupling element when the coupling element is rotated.

In some embodiments, the coupling element and/or setting element may have a catch element such as one or more snapper arms which are biased radially inwardly, for example, and are able to engage in teeth of the toothed-threaded rod to permit a rotating movement of the toothed-threaded rod relative to the dose setting element or coupling element in one direction and prevent it in the opposite direction.

In some preferred embodiments, a spring tensing element is provided, secured to the coupling element so as to rotate in unison with it and/or secured to the setting element so as to rotate in unison with it, which is rotated when the dose setting element is rotated. In this respect, a spring element, such as a helical spring or coiled leaf spring, may be provided between the spring tensing element and the guide element and may be connected to at least one of the elements permanently and to the other releasably so that the spring element can be tensed by a relative rotating movement between the spring tensing element and the guide element. Other options are to couple or connect the dose setting element directly with the spring tensing element or to make them as a single part.

In some preferred embodiments, the guide element is mounted in the dose setting device or injection device so that it is locked to prevent it from rotating when subjected to a torque acting in one direction, but is able to move in the opposite direction of rotation. To this end, one or more biased snapper arms directed outwardly may be provided, which engage in internal teeth of the dose setting device or injection device and thus produce an anti-rotation locking action on one side and/or in one direction. If the setting element can be moved in the axial direction, for example, the one-sided lock can be provided to prevent the translating movement.

In some embodiments, a trigger button or activator is provided, which can be pushed against the spring force or a force acting in the direction in which the trigger button is pushed in to release the coupling between the spring element and toothed-threaded rod so that the rod is no longer retained by snapper arms of the guide element but is still guided in the thread of the guide element. Thus, the spring, primed or tensed by rotating the dose setting sleeve during the setting operation, can be relaxed, thereby causing a rotating movement of the spring tensing element and optionally one of the elements coupled with it in a rotationally fixed arrangement relative to the guide element. The spring tensing sleeve and/or elements optionally connected to it in a rotationally fixed arrangement transmit this rotating movement via one or more snapper arms to the rod, which is moved in the axial direction, e.g. the distal direction of the injection device, as a result, guided in the dose setting element by the thread of the guide element.

In some embodiments, the present invention comprises an injection device incorporating a dose setting device of the type described herein.

In some preferred embodiments, the dose setting device, comprising the dose setting element, guide element and, optionally a coupling element and/or spring tensing element, can be rotated relative to the injection device in its entirety or with or by individual components. In this respect, the dose setting device may comprises one or at least two anti-rotation or one-way locks directed toward one side, which enable the element bearing the anti-rotation lock to be rotated in one direction and locked in the opposite direction.

Some embodiments of the present invention relate to a method of correcting or adjusting a dose set with a dose setting device, whereby the dose is set or adjusted by moving or rotating a dose setting element relative to a guide element and when correcting the dose, the guide element is moved or rotated with the dose setting element in the opposite direction by moving or rotating the dose setting element.

Another object of the present invention is to provide a spring element for an injection device, wherein the spring element can not be overloaded, distorted, damaged or destroyed by excessive tensioning. Thus, in some embodiments, the present invention comprises a system for securing a spring element to prevent excessive tensioning. In some embodiments, the system comprises a spring element and a spring retaining element, such as a guide element or a guide sleeve for example, which retains the spring relative to a dose setting device or the injection device. A spring tensing element, such as a spring tensing sleeve or a dose setting element serving as a spring tensing element may also be provided. The tensing element is used to tense the spring, and the spring element is disposed between the spring retaining element and the spring tensing element. Accordingly, the spring element may be non-releasably secured to at least one of these elements, in other words to the spring retaining element or to the spring tensing element. In accordance with some embodiments, one or more spring retaining regions are provided in the spring tensing element and/or spring retaining element, on or in which a retaining element of the spring can be releasably retained. The spring retaining element of the spring can be released from one of the spring retaining regions and move to an adjacent spring retaining region, but is retained if the spring element was deformed due to loading or tensing of the spring element and is thus at risk of damage.

In some embodiments, is also possible to provide only one spring retaining region so that if a cylindrical spring tensing element is used, for example, the spring can be relaxed by a full rotation if there is a risk of overload.

This makes it possible to prevent overload and hence damage to the spring, which is able to relax automatically if too strongly tensed.

In some embodiments, the retaining element of the spring may be a projecting portion, for example on an inner or outer end region of a coiled helical spring, which is able to engage in retaining regions based on a groove design.

In some preferred embodiments, if the spring element is connected to the spring retaining element at an inner region of the coiled spring for example, the at least one spring retaining region of the spring tensing element is disposed externally, in other words in the region in which a helical spring has a turn with a bigger or the biggest radius. In the case of the reverse arrangement, in which case the spring is retained externally, the spring retaining region may also be disposed internally, for example also inside the spring itself, and may be a cylindrical part-piece which has ridges or grooves on its circumference extending in the axial direction which serve as spring retaining regions.

In some embodiments, the present invention further relates to a means of securing a spring element to prevent excessive tensioning in a dose setting device of the type described herein and/or in an injection device of the type described herein.

In some embodiments, the present invention relates to a method of preventing a spring element, e.g. a helical spring, from being overloaded, the helical spring being fixedly connected to a spring retaining element and releasably connected to a spring tensing element, wherein the releasable connection is automatically released due to deformation of the spring in the event of too strong a tensing, thus ensuring that the spring is relaxed at least to a certain extent and reducing the chance or preventing overload and damage.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Figure 1A:
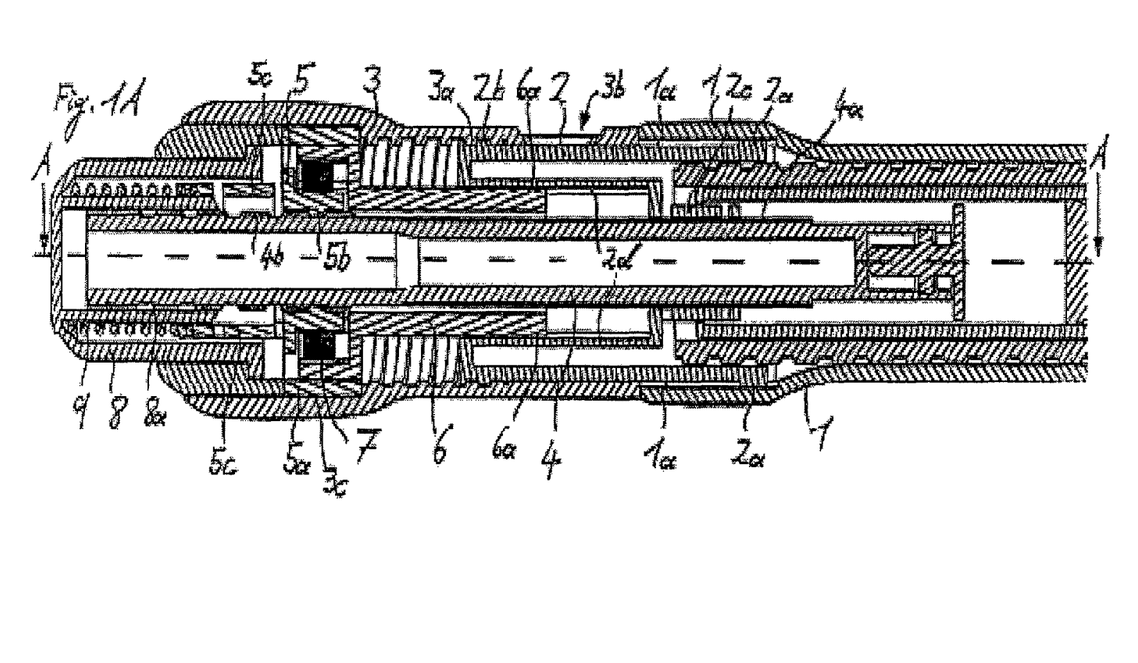
FIG. 1A is a cross-section through one embodiment of a dose setting device of one embodiment of an injection device.
Figure 1B:
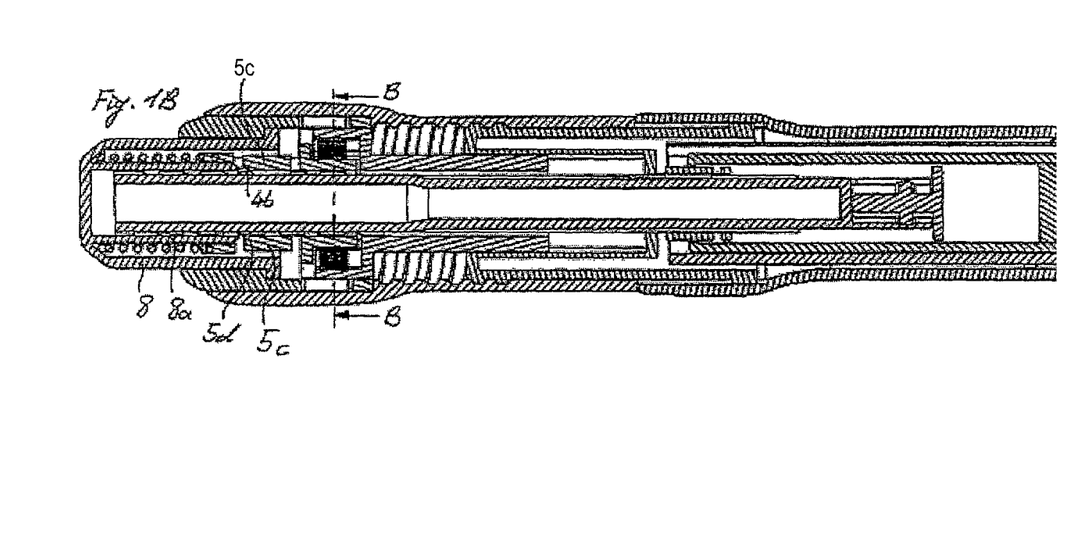
FIG. 1B is a cross section along line A-A of the dose setting device of FIG. 1A.
Figure 2:
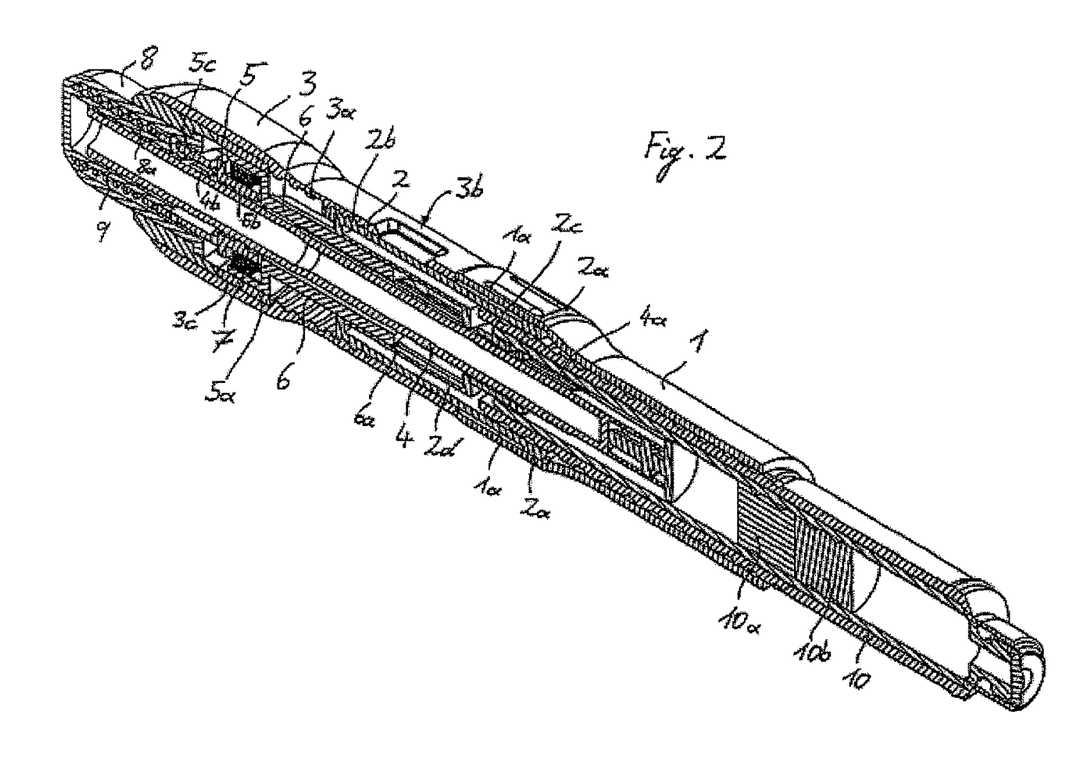
FIG. 2 is a perspective view in cross-section showing an injection device with the dose setting device illustrated in FIG. 1.

FIGS. 1A and 1B illustrate a dose setting unit of an injection device or an injection pen illustrated in FIG. 2, which is designed as a so-called automatic pen. Dispensing takes place automatically when the trigger button 8 is depressed due to a spring 7, which is pre-tensioned during the setting process, for example by turning the dose setting sleeve 1.

The dose setting sleeve 1 is mounted on or carried by a housing 3 of the injection device so that it is not able to move axially, but can be freely rotated.

On its internal face, the dose setting sleeve 1 has four grooves 1a extending in the axial direction, into which webs 2a extending radially outwardly from the display barrel 2 project. The display barrel 2 is therefore coupled with the dose setting sleeve 1 so that it is prevented rotating, but can be moved in the axial direction relative to the dose setting sleeve 1.

Disposed on the proximal or rear end of the display barrel 2 is an external thread 2b, which engages in an internal thread 3a of the housing 3. When the dose setting sleeve 1 is turned to set a dose, the dose setting sleeve 1 drives the display barrel 2 with it by the coupling (comprising elements 1a, 2a) which is screwed into the housing 3 in the proximal direction, guided by the thread (comprising elements 2b, 3a) when the dose is being set.

A viewing window 3b is provided in the housing 3, by which the set dose is displayed or visible and can be read from print applied to the external face of the display barrel 2.

The inwardly lying display barrel 2 fulfils the function of a rotating sleeve of a known type, and is provided with an inwardly biased snapper arm 2c which engages in toothing 4a of a toothed and/or threaded rod 4 guided inside the display barrel 2. The snapper arm 2c co-operates with the toothing 4a or a toothed thread of the rod 4. Thus, during an operation of setting or selecting the dose, when the toothed-threaded rod 4 is retained by a guide sleeve 5 by one or more snapper arms 5c biased radially inwardly which engage in the toothed thread 4b of the rod 4, the snapper arm 2c is moved out of engagement so that the display barrel 2 is able to rotate relative to the rod 4 and the snapper arm 2c is rotated about the rod 4 by several clicks or teeth in the circumference. However, the snapper arm 2c prevents a rotating movement in the opposite direction. The snapper arms 5c of the guide sleeve 5 may be of the same design as the snapper arms 2c of the display barrel 2, and have catch elements on resilient arms extending in the radial direction but act in the opposite direction with respect to the rod 4.

A spring tensing sleeve 6 is mounted in the injection device or housing 3 so that it is not able to move axially, but can be rotated. Disposed on the external face of the spring tensing sleeve 6 are webs 6a projecting radially outwardly. The webs 6a engage in radially extending guide grooves 2d on the internal face of the display barrel 2 so that a rotating movement of the display barrel 2 can be transmitted to the spring tensing sleeve 6. The display barrel 2 is locked to prevent it from rotating relative to the spring tensing sleeve 6, but can be moved in translation relative to it in the axial direction.

Provided on the internal face in the proximal region of the spring tensing sleeve 6 is a helical spring 7, which may be provided in the form of known torsion springs, coil springs, coiled leaf springs, clock springs, etc. The helical spring 7 is connected to the spring tensing sleeve 6 at the outer end and is connected to the guide sleeve 5 at the internal face.

When setting the dose, i.e. when rotating the dose setting sleeve 1, the guide sleeve 5 is locked by one or more snapper arms 5a biased radially outwardly and engaging in internal toothing 3d of the housing 3 to prevent a rotation relative to the injection device or housing 3 so that when the dose setting sleeve 1 moves in rotation, the helical spring 7 is tensed. Like the snapper arm connections 2c, 4a and 5c, 4b, the snapper arm coupling 5a, 3d establishes an anti-rotation lock in one direction only, e.g. a one-way lock, and permits a rotating movement in the opposite direction.

Unlike known pens, therefore, the guide sleeve 5 is not always coupled with the pen or housing 3 so that it is prevented from rotating and instead, it can be rotated in one direction, which is the direction opposite that used to increase or set the dose by using the dose setting sleeve 1. In a preferred embodiment, the guide sleeve 5 has two oppositely lying snapper arms 5a biased radially outwardly which engage in the internal toothing or longitudinal toothing 3c of the housing 3. Due to the snapper arms 5a, the guide sleeve 5 can therefore only be rotated in a direction of rotation specifically defined by the snapper arm profile, whereas a rotation in the opposite direction is blocked or prevented. The guide sleeve 5 has an internal thread 5b on the internal face, in which the external thread 4b of the rod 4 is guided. The snapper arms 5c provided on the guide sleeve 5 constitute a releasable anti-rotation lock element and engage in the teeth of the toothed thread 4b of the rod 4 so that the snapper arm 5c is coupled with the rod 4, and the rod 4 and guide sleeve 5 form a unit.

If too high a dose is set when rotating the dose setting sleeve 1, the dose setting sleeve 1 can be rotated in reverse or backward to adjust, i.e. reduce or correct, the dose. During the backward rotating movement, the dose setting sleeve 1, display barrel 2, spring tensing sleeve 6, toothed-threaded rod 4 and guide sleeve 5 are coupled or locked together to form a unit locked so as to rotate in unison. In particular, due to the anti-rotation lock 1a, 2a and the snapper arm 2c of the display barrel 2, the dose setting sleeve 1 is coupled so that it rotates in unison with the rod 4, which is also rotated backward when the dose setting sleeve 1 is rotated backward. During this backward rotating movement, however, the rod 4 is not moved in the axial direction. The guide sleeve 5 is coupled by the snapper arms 5c with the rod 4 so as to rotate in unison with it and is, therefore, also driven by the eaded rod 4 during the backward rotating movement. The guide sleeve 5 therefore rotates relative to the housing 3 of the injection device.

Due to the fact that the guide sleeve 5 and spring tensing sleeve 6 do not effect a relative rotating movement, the helical spring 7 remains tensed. If the injection device were to be operated several times by rotating the dose setting sleeve 1 backward and forward to set and correct a dose, the helical spring 7 would remain tensed.

Figure 3A:
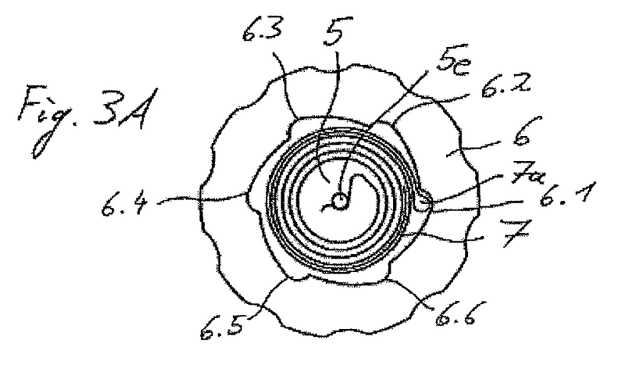
FIG. 3A is a cross-section along line B-B indicated in FIG. 1B illustrating one embodiment of a securing means for preventing an overload.
Figure 3B:
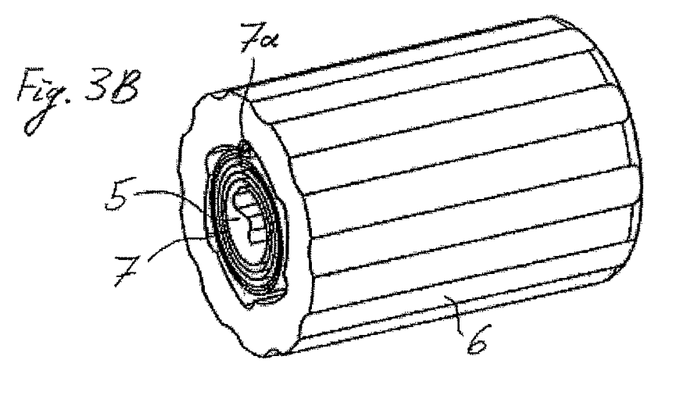
FIG. 3B is a perspective view of the tensing mechanism secured to prevent an overload.

To prevent the helical spring 7 from being excessively tensed, use is made of the fact that a helical spring 7, which is permanently secured in the middle or on the internal face of a spring holder 5e of the guide sleeve 5, has an increasingly small external diameter as it is tensed. In the outer end region, the helical spring 7 has a coupling element 7a, as illustrated in FIG. 3, which is retained on the internal face of the spring tensing sleeve 6 in one of several possible holding positions 6.1, 6.2, 6.3, 6.4, 6.5 or 6.6.

The holding positions 6.1-6.6 may be obtained by axially extending grooves in which a bulge, protrusion or a thickened end 7a on the outer end of the helical spring 7 engages. If the helical spring 7 is tensed to the degree that the external diameter has decreased to the point that the outer protrusion 7a of the helical spring 7 is pushed back out of the groove 6.1 of the spring tensing sleeve 6 in the axial direction, the helical spring 7 will automatically relax, causing the retaining element 7a to slide further inside the spring tensing sleeve 6 by one holding position into position 6.2. The automatic relaxing mechanism described above therefore prevents the helical spring 7 from being overloaded.

For actuating or triggering purposes, a trigger button 8 is pushed in the distal direction of the injection device against the force of an axially acting spring 9. On the internal face, the trigger button 8 has arms projecting inwardly in the axial direction or a cylinder 8a with a conically converging design at its front end face. The conical region of the cylinder 8a engages on an oblique contact surface 5d of the snapper arms 5c of the guide sleeve 5, as illustrated in FIG. 1B, and lifts it radially outwardly so that the coupling between the snapper arms 5c and the rod 4 is released.

During dispensing, the guide sleeve 5 is connected to the housing 3 of the injection device by the snapper arms 5a so that it rotates in unison with it. The helical spring 7 tensed between the guide sleeve 5 and the spring tensing sleeve 6 therefore generates a torque on the spring tensing sleeve 6, which transmits the torque to the display barrel 2, which is locked to prevent rotation, and the dose setting sleeve 1 connected to the display barrel 2, which is locked to prevent rotation, and the rotating movement of the display barrel 2 is transmitted by the snapper arm 2c to the rod 4, which is screwed in the distal direction relative to the guide sleeve 5 by the internal thread 5b of the guide sleeve 5 and thus produces a forward movement. As the helical spring 7 relaxes, the display barrel 2 is rotated backward at the same time. A new setting operation can then be started using the dose setting sleeve 1 again.

It should be understood that the described dose setting and injection device may be used to dispense a measured dose from a standard ampoule or a two-chamber ampoule 10, as illustrated in FIG. 2. Accordingly, the two-chamber ampoule 10 is screwed into the injection device in a known manner prior to administering a dose, so that the proximal stopper 10a is pushed in the direction toward the distal stopper 10b so that the fluid contained in the volume between stoppers 10a and 10b is mixed with the fluid disposed at the distal end of the stopper 10b before the start of an injection.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A dose setting device for an injection device for administering a substance, the dose setting device being for setting or correcting or reducing an amount of the substance to be administered and comprising a dose setting element which can be rotated in a first direction to set a dose and rotated in an adjusting direction opposite to the first direction to correct or reduce the set dose, and a guide element for guiding a threaded rod, wherein the dose setting element is rotated relative to the guide element to set the dose, and wherein when the dose setting element is rotated in the adjusting direction opposite to the first direction to correct or reduce the set dose the guide element is also rotated in the adjusting direction opposite to the first direction, said dose setting device further comprising a coupling element coupled with the dose setting element to rotate in unison with the dose setting element in the adjusting direction, and which has an anti-rotation lock mechanism acting on one side to establish an anti-rotation lock of the coupling element to the threaded rod in the adjusting direction, whereas rotation of the coupling element relative to the threaded rod in a direction opposite the adjusting direction is possible.

2. The dose setting device as claimed in claim 1, wherein the rod has at least one of a toothed thread, a toothed thread portion, and a toothed region.

3. The dose setting device as claimed in claim 1, wherein the coupling element comprises a thread which can be guided in the dose setting device or the injection device.

4. The dose setting device as claimed in claim 3, further comprising a spring tensing element coupled with at least one of the coupling element and the dose setting element to rotate in unison therewith.

5. The dose setting device as claimed in claim 4, further comprising a spring element retained between the guide element and the spring tensing element.

6. The dose setting device as claimed in claim 5, wherein the spring element is releasably or non-releasably connected to at least one of the guide element and the spring tensing element.

7. The dose setting device as claimed in claim 1, wherein the guide element comprises at least one anti-rotation lock element to permit a relative rotation of the threaded rod and the guide element when the dose setting element rotates in the first direction and block the relative rotation of the threaded rod and the guide element when the dose setting element rotates in the adjusting direction.

8. The dose setting device as claimed in claim 1, wherein the guide element has at least one anti-rotation lock element to permit a rotation of the guide element relative to the dose setting device or relative to the injection device in the adjusting direction and block the relative rotation of the guide element in an opposite direction.

9. The dose setting device as claimed in claim 1, further comprising a trigger element by which the anti-rotation lock mechanism between the coupling element and the threaded rod can be released.

* * * * *